United States Patent [19]

Gulko

[11] 4,402,696
[45] Sep. 6, 1983

[54] FOLDED APPLICATOR

[76] Inventor: Bruce N. Gulko, 1835 Arcola Ave., Silver Spring, Md. 20902

[21] Appl. No.: 84,567

[22] Filed: Oct. 15, 1979

[51] Int. Cl.³ .............................................. A61M 7/00
[52] U.S. Cl. .................................................... 604/897
[58] Field of Search .............. 128/155, 156, 260, 268; 401/132, 7

[56] References Cited

U.S. PATENT DOCUMENTS

| | | | |
|---|---|---|---|
| 2,389,870 | 11/1945 | Reevely | 128/156 |
| 2,928,389 | 3/1960 | Ganz et al. | 128/156 |
| 3,280,420 | 10/1966 | Wanzenberg | 401/7 |
| 3,339,546 | 9/1967 | Chen | 128/268 |
| 3,363,625 | 1/1968 | Jovis | 128/260 |
| 3,906,951 | 9/1975 | Chen | 128/260 |
| 3,996,934 | 12/1976 | Zaffaroni | 128/260 |
| 4,053,053 | 10/1977 | Tumangday | 128/155 |

FOREIGN PATENT DOCUMENTS 2333633  7/1973  Fed. Rep. of Germany ...... 401/132

Primary Examiner—Richard J. Apley
Assistant Examiner—T. J. Wallen
Attorney, Agent, or Firm—Arnold G. Gulko

[57] ABSTRACT

An applicator for applying an active agent to a living surface is provided in which a strip of film has a peripheral portion on one side thereof coated with pressure sensitive adhesive, the adhesive surrounding a central portion which carries a liquid containing an active agent. The strip is folded upon itself and held in the folded position by the pressure sensitive adhesive to confine said active agent and prevent its contamination. Also, the strip has flaps uncoated with pressure sensitive adhesive extending beyond the adhesive-coated portion to facilitate opening the folded strip without contacting the active agent.

7 Claims, 2 Drawing Figures

FOLDED APPLICATOR

DESCRIPTION

1. Technical Field

This invention relates to an applicator for applying an active agent, such as a medicine, herbicide, systemic pesticide or fungicide, or the like, to a living surface, such as skin, hide or bark.

2. Background Art

The application of medicines to humans and animals, and the treatment of trees and shrubs with various agents is well known. It is desired to simplify such application in various ways. First, it is desired that the applicator structure be inexpensive. Second, it is desired that the active agent be protected by the applicator structure to prevent its becoming contaminated by extraneous material or from losing its potency, as by exposure to dirt or air. Third, it is desired to enable simplified and rapid application and to enable this to be accomplished without contact between the active agent and any portion of the person doing the applicating. Also, and especially when the applicator is applied to a tree or shrub, it is desired to form the applicator in such a manner that the entire applicator is applied and, preferably also, that it need not be removed, so as to eliminate the problem of disposing of contaminated material.

DISCLOSURE OF INVENTION

In accordance with this invention, an applicator for applying an active agent to a living surface comprises a strip of film having a peripheral portion on one side thereof coated with a pressure sensitive adhesive, this adhesive surrounding a central portion carrying an active agent, preferably in the form of a coating of viscous liquid. This strip is folded upon itself to confine the active agent and prevent its contamination. In many instances the active agent can be dangerous, so the fact that it is confined between the folded over portions of the film and entrapped by the pressure sensitive adhesive which surrounds it also serves to prevent inadvertent contact between the active agent and the public which desires to use the applicator.

When the applicator is unfolded and applied to a living surface, the entire applicator including the flaps which facilitate opening, is applied, and nothing which may have contacted the active agent need be kept around where it might injure persons or present a disposal problem. In preferred practice where the applicator is applied to a tree or shrub, the film is made of a water soluble polymer so that it dissolves over a period of time. In this way, the applicator need not be removed from the tree or shrub which entirely eliminates the disposal problem.

Various features of the invention will become evident from a description of some preferred forms of the invention which are illustrated in the accompanying drawings.

BEST MODE FOR CARRYING OUT THE INVENTION

Figure 1:
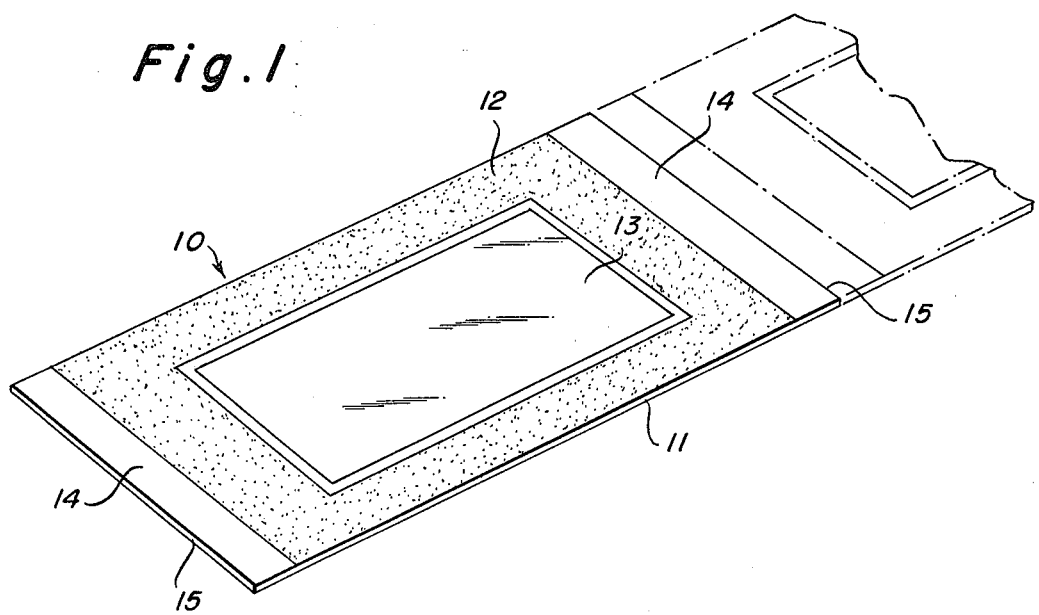
FIG. 1 is a perspective view showing an applicator blank constructed in accordance with the invention.

Referring more particularly to FIG. 1, the numeral 10 identifies an applicator blank constituted by a strip of impermeable film 11 having a peripheral portion 12 on one side thereof coated with a pressure sensitive adhesive. The peripheral portion 12 surrounds a central area 13 which is coated with a liquid containing an active agent. Uncoated portions 14 extend beyond the portion coated with pressure sensitive adhesive, and these uncoated portions will eventually form flaps to enable handling of the applicator while it is unfolded and secured in place by pressing the adhesive-coated surface of the unfolded applicator against the living surface which it is desired to treat.

It will be seen that blank 10 is one of a series of blanks which extend along the length of the film strip 11. The next blank is shown with phantom lines, and after the strip 11 is coated with pressure sensitive adhesive and liquid containing active agent, the blanks are cut apart in the center of an uncoated portion 14 along the line 15. The blanks may be cut apart before or after folding. After folding, the cut may be incomplete so that the folded blanks remain connected for severance at the time of application.

Figure 2:
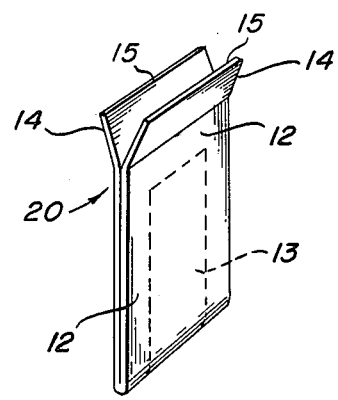
FIG. 2 is a perspective view showing the applicator blank of FIG. 1 folded to produce an applicator structure in which the active agent is surrounded by pressure sensitive adhesive to confine the active agent and prevent its contamination.

When the blank of FIG. 1 is folded upon itself with the lines of pressure sensitive adhesive coming together as shown in FIG. 2, this provides an applicator 20, the fold line being shown at 16. As will now be evident, active agent is entirely confined by the film 11 and by the pressure sensitive adhesive 12 so that it cannot be contaminated or come into contact with anyone handling the applicator. The flaps 14 provide finger grips, and when these are pulled, the applicator blank structure shown in FIG. 1 is restored, ready to be applied to the living surface which is to be treated.

In preferred practice, the active agent is in the form of a viscous liquid which is coated upon the film, but it can also be coated upon another film which better resists the liquid, this other film being adhered to the film which constitutes the applicator.

The active agent is subject to wide variation, but it is particularly desired to employ a systemic fungicide or pesticide which is liquified by the presence of a small amount of organic solvent. The volatilization of this solvent is prevented because the active agent liquid is trapped between the folded over film and confined by the pressure sensitive adhesive which surrounds it. A particularly preferred solvent is dimethyl sulfoxide which assists the active agent in penetrating the living surface. The preferred film for horticultural use is carboxy methyl cellulose which is sufficiently water-soluble so that it will dissolve away from a tree or shrub to which it is applied as rain washes the film over a period of time. Polyvinyl chloride is also useful for the film, and it is strongly resistant to the action of most organic solvents.

Figure 3:
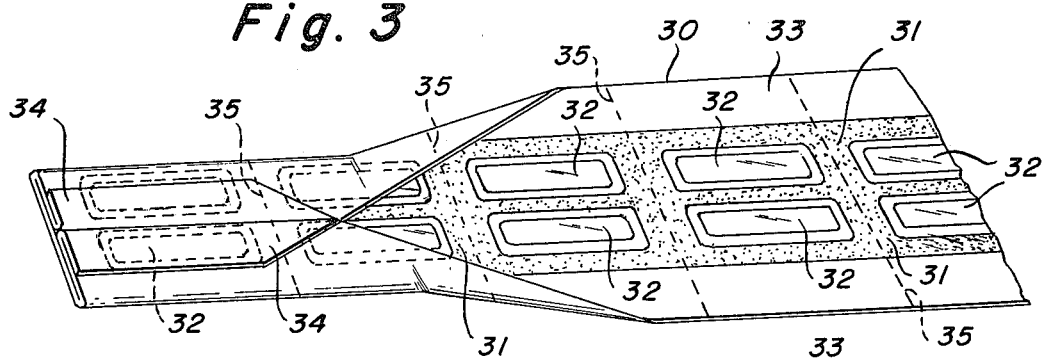

In the structure shown in FIG. 3, the film 30 is advanced from right to left and is imprinted with a pattern of pressure sensitive adhesive 31 surrounding islands of active agent 32. The side margins 33 are left uncoated, and these are folded inwardly and then outwardly to cover the adhesive-coated areas and the active agent areas and to provide flaps 34. Either prior to or after folding, the film 30 can be perforated along lines 35 to allow subsequent separation into individual applicators.

EXAMPLE 1

A strip of polyvinyl chloride film is coated with pressure sensitive adhesive as shown in FIG. 1 and the central portion 13 is then coated with a film of a viscous paste formed by mixing 90 parts of the systemic pesticide o,o,diethyl S-[2-(ethylthio)ethyl]phosphorodithioate with 10 parts of hexane. The coated film is then folded as shown in FIG. 2 and is ready for use.

The hexane can be replaced in whole or in part with dimethyl sulfoxide or ethyl alcohol.

The polyvinyl chloride film can be replaced with a carboxy methyl cellulose film.

The pesticide used in this example is merely illustrative, but other typical systemic pesticides requiring careful handling are illustrated by the commercial materials, Temix and Meta Syston A. A suitable fungicide is available under the tradename Benelate.

I claim:

1. An applicator for applying an active agent to a living surface comprising a strip of film having a peripheral portion on one side thereof coated with pressure sensitive adhesive, said adhesive surrounding a central portion carrying a liquid containing an active agent, said strip being folded upon itself and held in said folded position by said pressure sensitive adhesive to confine said active agent and prevent its contamination, and said film having flaps uncoated with pressure sensitive adhesive extending beyond the portion thereof which is coated with said adhesive at both ends of said strip remote from the fold therein to facilitate opening said folded strip, and said strip, when unfolded, may be grasped by said uncoated flaps and adhesively attached to said living surface with said pressure sensitive adhesive.

2. An applicator as recited in claim 1 in which said film is water-soluble.

3. An applicator as recited in claim 1 in which said active agent is a systemic fungicide or pesticide.

4. An applicator as recited in claim 1 in which said active agent is in viscous solution in an organic solvent.

5. An applicator as recited in claim 4 in which said organic solvent comprises dimethyl sulfoxide.

6. An applicator as recited in claim 1 in which said film is constituted by carboxy methyl cellulose.

7. An applicator as recited in claim 1 in which said film is constituted by polyvinyl chloride.

* * * * *